US011103308B2

(12) United States Patent
Brannan

(10) Patent No.: US 11,103,308 B2
(45) Date of Patent: Aug. 31, 2021

(54) REUSABLE TRANSMISSION NETWORK FOR DIVIDING ENERGY AND MONITORING SIGNALS BETWEEN SURGICAL DEVICES

(71) Applicant: COVIDIEN LP, Mansfield, MA (US)

(72) Inventor: Joseph D. Brannan, Lyons, CO (US)

(73) Assignee: Covidien LP, Mansfield, MA (US)

( * ) Notice: Subject to any disclaimer, the term of this patent is extended or adjusted under 35 U.S.C. 154(b) by 933 days.

(21) Appl. No.: 15/837,495

(22) Filed: Dec. 11, 2017

(65) Prior Publication Data
US 2019/0175270 A1    Jun. 13, 2019

(51) Int. Cl.
*A61B 18/18* (2006.01)
*H01P 5/12* (2006.01)
(Continued)

(52) U.S. Cl.
CPC ...... *A61B 18/1815* (2013.01); *A61B 18/1477* (2013.01); *G16H 40/63* (2018.01); *H03H 11/22* (2013.01); *H05B 6/68* (2013.01); *A61B 2017/00084* (2013.01); *A61B 2017/00123* (2013.01); *A61B 2017/00482* (2013.01);
(Continued)

(58) Field of Classification Search
CPC ........ H01P 5/12; A61B 18/18; A61B 18/1818
See application file for complete search history.

(56) References Cited

U.S. PATENT DOCUMENTS

| 3,941,121 A | 3/1976 | Olinger et al. |
| 3,941,924 A | 3/1976 | Leiboff |

(Continued)

FOREIGN PATENT DOCUMENTS

| EP | 0219216 A1 | 4/1987 |
| WO | 8301902 A1 | 6/1983 |

(Continued)

OTHER PUBLICATIONS

International Search Report and Written Opinion of the International Searching Authority issued in corresponding Appl. No. PCT/US18/63965 dated Feb. 12, 2019 (16 pages).

*Primary Examiner* — Dean O Takaoka
(74) *Attorney, Agent, or Firm* — Carter, DeLuca & Farrell LLP

(57) ABSTRACT

Microwave ablation systems and methods use a cable assembly including a signal divider device that enables use of multiple microwave antennas through a single channel of a microwave generator. The cable assembly includes a microwave transmission line, a signal divider device having multiple ports coupled to an end portion of the microwave transmission line, an electrical line, and a monitoring circuit coupled to an end portion of the electrical line. The monitoring circuit is configured to acquire information regarding multiple devices coupled to multiple respective ports of the signal divider device and convert the information regarding multiple devices to single channel information. The single channel information is inserted in a communication packet and transmitted to the microwave generator via the electrical line. The signal divider device includes a temperature sensor, which the monitoring circuit monitors to ensure that the temperature of the signal divider device circuitry remains within temperature limits.

11 Claims, 11 Drawing Sheets

(51) Int. Cl.
*A61B 18/14* (2006.01)
*H05B 6/68* (2006.01)
*G16H 40/63* (2018.01)
*H03H 11/22* (2006.01)
*A61B 17/00* (2006.01)
*A61B 18/00* (2006.01)

(52) U.S. Cl.
CPC ............... *A61B 2018/00577* (2013.01); *A61B 2018/00678* (2013.01); *A61B 2018/00708* (2013.01); *A61B 2018/00791* (2013.01); *A61B 2018/00821* (2013.01); *A61B 2018/00988* (2013.01); *A61B 2018/1425* (2013.01); *A61B 2018/1823* (2013.01); *A61B 2018/1869* (2013.01)

(56) References Cited

U.S. PATENT DOCUMENTS

| | | | |
|---|---|---|---|
| 4,182,996 A | 1/1980 | Spence | |
| 4,292,960 A | 10/1981 | Paglione | |
| 4,311,154 A | 1/1982 | Sterzer et al. | |
| 4,312,364 A | 1/1982 | Convert et al. | |
| 4,336,809 A | 6/1982 | Clark | |
| 4,397,314 A | 8/1983 | Vaguine | |
| 4,448,198 A | 5/1984 | Turner | |
| 4,632,128 A | 12/1986 | Paglione et al. | |
| 4,669,475 A | 6/1987 | Turner | |
| 4,672,980 A | 6/1987 | Turner | |
| 4,676,258 A | 6/1987 | Inokuchi et al. | |
| 4,741,348 A | 5/1988 | Kikuchi et al. | |
| 4,785,829 A | 11/1988 | Convert et al. | |
| 4,815,479 A | 3/1989 | Carr | |
| 4,860,752 A | 8/1989 | Turner | |
| 4,907,589 A | 3/1990 | Cosman | |
| 4,994,062 A | 2/1991 | Nishigaki et al. | |
| 5,023,945 A | 6/1991 | Childs | |
| 5,097,844 A | 3/1992 | Turner | |
| 5,122,137 A | 6/1992 | Lennox | |
| 5,197,466 A | 3/1993 | Marchosky et al. | |
| 5,220,927 A | 6/1993 | Astrahan et al. | |
| 5,249,585 A | 10/1993 | Turner et al. | |
| 5,269,780 A | 12/1993 | Roos | |
| 5,273,524 A | 12/1993 | Fox et al. | |
| 5,312,392 A | 5/1994 | Hofstetter et al. | |
| 5,334,193 A | 8/1994 | Nardella | |
| 5,354,325 A | 10/1994 | Chive et al. | |
| 5,403,311 A | 4/1995 | Abele et al. | |
| 5,417,687 A | 5/1995 | Nardella et al. | |
| 5,419,767 A | 5/1995 | Eggers et al. | |
| 5,484,400 A | 1/1996 | Edwards et al. | |
| 5,496,312 A | 3/1996 | Klicek | |
| 5,540,681 A | 7/1996 | Strul et al. | |
| 5,542,916 A | 8/1996 | Hirsch et al. | |
| 5,630,426 A | 5/1997 | Eggers et al. | |
| 5,810,802 A | 9/1998 | Panescu et al. | |
| 6,208,903 B1 | 3/2001 | Richards et al. | |
| 6,346,104 B2 | 2/2002 | Daly et al. | |
| 6,347,251 B1 | 2/2002 | Deng | |
| 7,128,739 B2 | 10/2006 | Prakash et al. | |
| 7,197,363 B2 | 3/2007 | Prakash et al. | |
| 7,294,127 B2 | 11/2007 | Leung et al. | |
| 8,641,704 B2 | 2/2014 | Werneth et al. | |
| 9,095,359 B2 | 8/2015 | Behnke, II et al. | |
| 2006/0200120 A1 | 9/2006 | DiCarlo et al. | |
| 2008/0147056 A1 | 6/2008 | van der Weide et al. | |
| 2009/0299157 A1 | 12/2009 | Telfort et al. | |
| 2009/0318793 A1 | 12/2009 | Datta et al. | |
| 2009/0326620 A1 | 12/2009 | Rossetto et al. | |
| 2010/0030206 A1 | 2/2010 | Brannan et al. | |
| 2011/0071512 A1* | 3/2011 | Behnke, II | A61B 18/1815 606/33 |
| 2011/0118723 A1 | 5/2011 | Turner et al. | |
| 2012/0016360 A1 | 1/2012 | Brannan | |
| 2013/0192063 A1* | 8/2013 | Brannan | A61B 18/1815 29/825 |
| 2014/0276739 A1* | 9/2014 | Brannan | A61B 34/25 606/33 |
| 2015/0173834 A1* | 6/2015 | Brannan | A61B 18/1815 606/33 |
| 2016/0228186 A1 | 8/2016 | Hancock et al. | |
| 2016/0256219 A1* | 9/2016 | Lee | A61B 18/1815 |

FOREIGN PATENT DOCUMENTS

| | | |
|---|---|---|
| WO | 9300958 A1 | 1/1993 |
| WO | 9423794 A1 | 10/1994 |
| WO | 9525472 A1 | 9/1995 |
| WO | 9629946 A1 | 10/1996 |
| WO | 9706727 A1 | 2/1997 |

\* cited by examiner

REUSABLE TRANSMISSION NETWORK FOR DIVIDING ENERGY AND MONITORING SIGNALS BETWEEN SURGICAL DEVICES

BACKGROUND

When other treatments like resection, embolization, and chemotherapy are not an option for a patient or a patient looking for combined treatments, ablation provides a minimally invasive solution. However, many current ablation technologies do not give clinicians confidence that they have ablated an entire targeted lesion and failure to fully ablate could increase the chances of recurrence. Predictable ablation systems have been developed to provide three kinds of spatial energy control: thermal, field, and wavelength. This technology maintains a predictable spherical ablation zone throughout a procedure and brings confidence to ablation procedures including the ablation of liver tumors and other soft tissue within the body.

Many ablation systems are single needle systems. The single needle systems are preferred for 3 cm or smaller lesions and are used to address small spherical tumors, but may not be optimal for planar coagulation. Planar coagulation typically involves two or more needles energized simultaneously.

SUMMARY

The present disclosure features multi-channel ablation systems which include one microwave generator (e.g., a 2450 MHz, 150 W generator), a multi-channel reusable cable (e.g., a two-channel reusable cable) and a multi-antenna cooling system (e.g., a dual-antenna cooling system). A multi-channel reusable cable may expand to larger tumor ablations (e.g., 4 cm or more). Moreover, the multi-channel ablation system enables users to address larger non-spherical tumors and to place multiple ablation devices prior to energy delivery for needle guidance.

In aspects, this disclosure features a cable assembly. The cable assembly includes a microwave transmission line, a signal divider network, an electrical line, and a monitoring circuit. The signal divider network includes at least two ports and is coupled to an end portion of the microwave transmission line. The monitoring circuit is coupled to the electrical line and receives at least first and second device information via the at least two ports and converts the at least first and second device information to single channel information.

In aspects, the cable assembly is a reusable cable assembly. In aspects, the signal divider network includes a power splitter.

In aspects, the cable assembly includes a temperature sensor that measures the temperature of the power splitter. The monitoring circuit is in communication with the temperature sensor, monitors the temperature of the power splitter, and transmits a power splitter temperature message to a microwave generator if the temperature of the power splitter exceeds a predetermined temperature threshold.

In aspects, the cable assembly includes a phase shifter that shifts the phase of the divided microwave energy to produce microwave signals that are in phase.

In aspects, the power splitter is a passive power splitter that divides microwave energy equally between the at least two ports.

In aspects, the first and second device information include identification information and status information corresponding to respective devices connected to respective ports.

In aspects, the status information includes the temperature of each of at least two microwave antennas connected to the at least two ports.

In aspects, the single channel information is backward compatible with a single channel generator.

In aspects, the cable assembly includes a switch that switches between a single channel cable and a double channel cable.

In aspects, this disclosure also features a method of performing an ablation procedure. The method includes receiving at least first and second device information; converting the at least first and second device information to single channel information; and transmitting the single channel information via communication lines disposed within a cable. The method further includes extracting the at least first and second device information from the single channel information; analyzing the at least first and second device information; generating and transmitting an enable signal in response to the analysis; and generating and transmitting a microwave power signal. The method further includes dividing the microwave signal into at least first and second microwave power signals; and allowing propagation of the at least first and second microwave power signals to respective first and second microwave antennas in response to receiving the enable signal.

In aspects, the first and second device information includes temperature measurements of the first and second microwave antennas, and the method includes cooling the first and second microwave antennas using a fluid based on the temperature measurements of the first and second microwave antennas.

In aspects, dividing the microwave signal is performed by a power splitter, and the method includes sensing a temperature of the power splitter, determining whether the temperature of the power splitter is greater than a predetermined temperature threshold, transmitting a high-temperature notification message if the temperature of the power splitter exceeds the predetermined temperature threshold, and stopping the generating of a microwave power signal in response to receiving the high-temperature notification message.

In aspects, the method includes synchronizing the phase of the first and second microwave power signals using a phase shifter disposed in the signal divider device.

In aspects, the method includes receiving first and second electromagnetic location tracking signals from the first and second microwave antennas, respectively, converting the first and second electromagnetic location tracking signals to first and second location tracking data, respectively, and transmitting the first and second location tracking data to a navigation system running on a microwave generator.

This disclosure also features a microwave ablation system. The microwave ablation system includes a microwave generator, a cable assembly, and at least two microwave antennas. The microwave generator has a microwave power source that generates microwave energy. The cable assembly includes a microwave transmission line, a signal divider network connected to an end portion of the microwave transmission line and including at least two ports, and a signal divider circuit that receives at least first and second device information via the at least two ports, respectively, and converts the at least first and second device information into single channel information. The at least two microwave antennas are connected to the at least two ports, respectively. Each microwave antenna converts each respective divided portion of the microwave energy into respective microwave fields.

In aspects, the first and second device information includes identification information and status information corresponding to the devices connected to the at least two ports.

In aspects, the status information includes the temperature of each of the at least two microwave antennas, and the generator controls a parameter of the microwave energy based on the temperature of each of the at least two microwave antennas.

In aspects, the generator includes a transfer switch that switches between a single channel cable and a double channel cable.

In aspects, the first and second device information is first and second identification information of the two respective microwave antennas. The signal divider circuit transmits the single channel information to a communication circuit of the generator. The communications circuit extracts the first and second identification information from the single channel information and transmits a single message requesting operational parameters of the first and second microwave antennas. The signal divider circuit acquires first and second operational parameters from respective first and second microwave antennas in response to receiving the single request message, generates a single channel response message including the first and second operational parameters, and transmits the single channel response message to the communication circuit of the generator.

BRIEF DESCRIPTION OF THE DRAWINGS

Various aspects of the present disclosure are described below with reference to the drawings, wherein.

DETAILED DESCRIPTION

Figure 1:
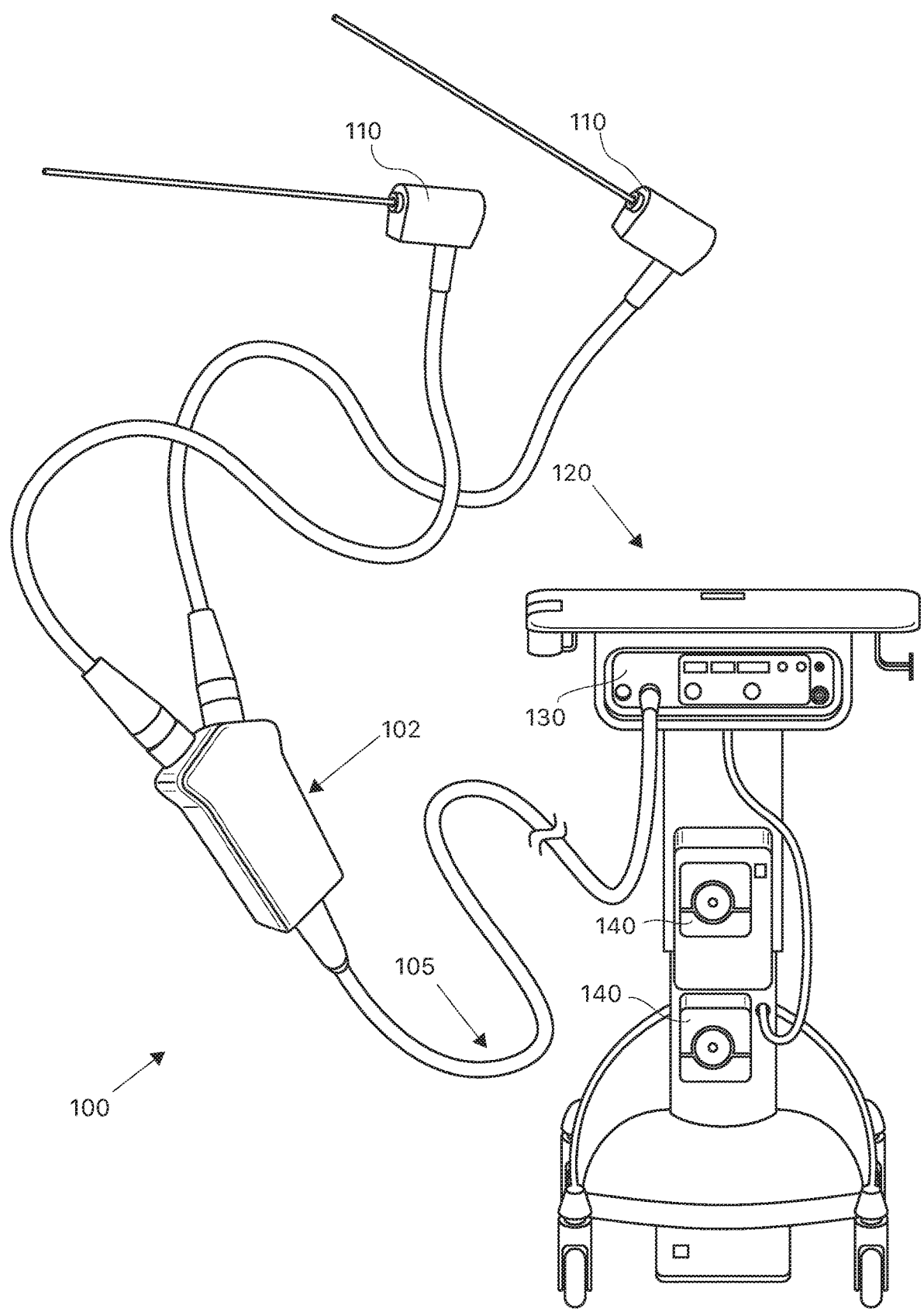
FIG. 1 is a perspective view of a microwave ablation system according to embodiments.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the phrase "in embodiments" and variations on this phrase generally is understood to mean that the particular feature, structure, system, or method being described includes at least one iteration of the disclosed technology. Such phrase should not be read or interpreted to mean that the particular feature, structure, system, or method described is either the best or the only way in which the embodiment can be implemented. Rather, such a phrase should be read to mean an example of a way in which the described technology could be implemented, but need not be the only way to do so.

This disclosure generally pertains to a microwave cable assembly for multiple microwave antennas. In particular, this disclosure relates to systems and methods for dividing microwave energy, which has been provided through a single channel of a microwave generator, between multiple microwave antennas and monitoring the microwave antennas through the single channel of the microwave generator. The microwave cable assembly includes a cable that can be connected to a microwave generator and a microwave connector assembly that can be connected to multiple microwave antennas. The microwave cable assembly includes circuitry that obtains identification, configuration, and/or status information from the multiple microwave antennas and converts this information into single channel information. The single channel information is in a format that can be transmitted to the microwave generator via a single channel port and read by the microwave generator. The microwave generator may then parse the single channel information to obtain the information regarding the multiple microwave antennas. This information may then be used by the microwave generator to adjust one or more characteristics of the microwave power signal generated by the microwave generator or perform further communications and/or interactions with the microwave antennas.

FIG. 1 illustrates a microwave ablation system, which includes a microwave generator 130 and a cooling system 140 including two fluid pumps. The microwave generator 130 and the cooling system are configured to operate with multiple disposable antennas 110, which can be coupled to the generator 130 and the cooling system 140 via a reusable cable assembly 100. The reusable cable assembly 100 includes a double barrel connector assembly 102 and a cable 105 including a microwave transmission line and a communications line. The microwave ablation system may also include one or more optional remote temperature probes.

Figure 2:
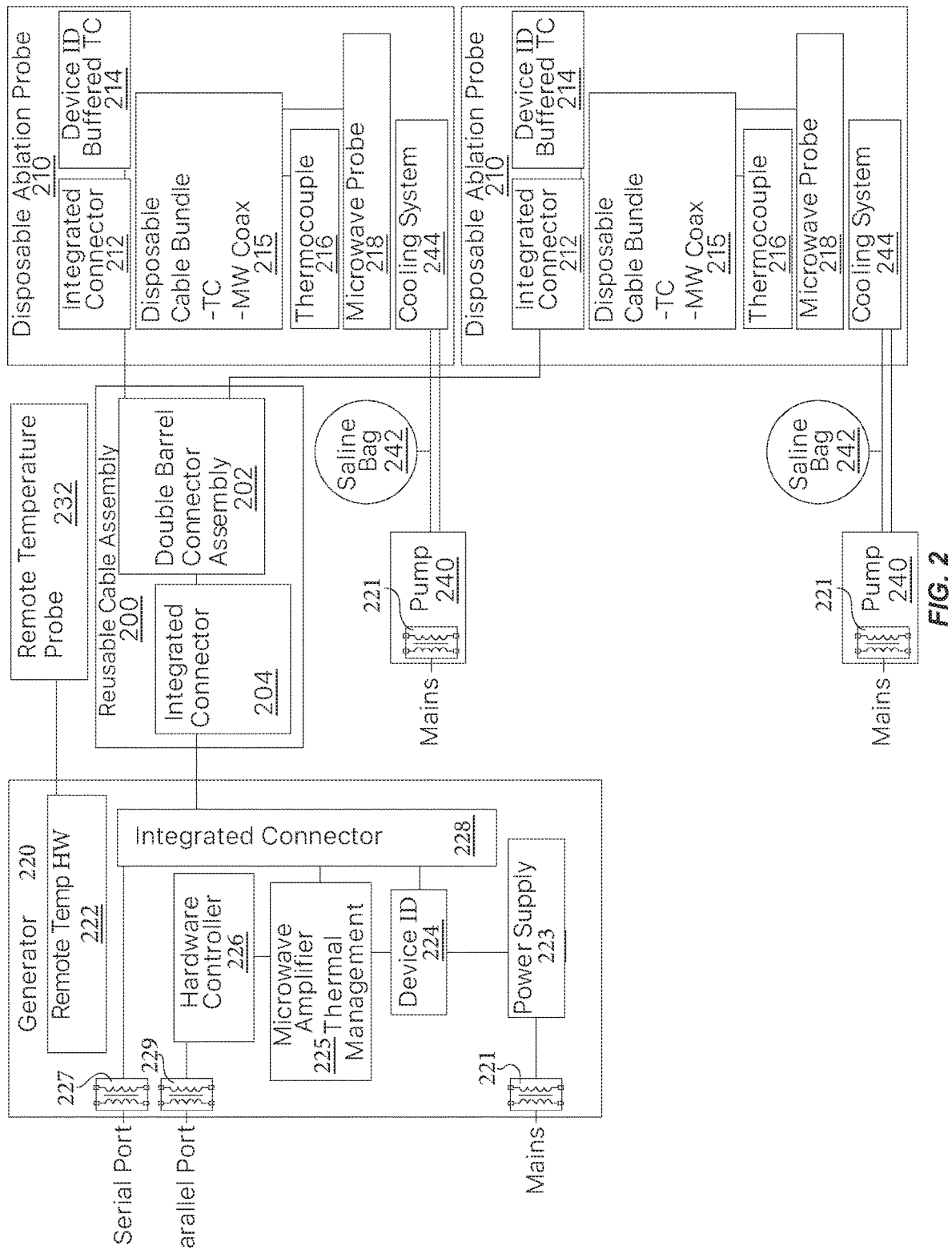
FIG. 2 is a block diagram of a microwave ablation system illustrating a cable assembly including a double barrel connector assembly connected between a microwave generator and multiple ablation probes according to embodiments.

FIG. 2 is a block diagram of a microwave ablation system. The microwave ablation system includes a microwave generator 220, a remote temperature probe 232 coupled to the generator 220, two disposable ablation probes 210 coupled to the microwave generator 220 via a reusable cable assembly 200, and two fluid pumps and saline bags coupled to corresponding disposable ablation probes 210.

Each ablation probe 210 includes an integrated connector 212, a memory 214 for storing device identification information and buffered thermocouple information, a cable bundle 215 including a coaxial cable and electrical lines, a thermocouple 216, a microwave probe 218, and a cooling system 244. The electrical lines may include any combination of the following lines: a thermocouple line, a device identification voltage sense line (e.g., a Vsense line), one or more I/O digital communication lines, a power line (e.g., Vsource), a ground (GND) line, and a precision voltage reference line (e.g., a Vref line). The electrical lines of the cable bundle 215 are connected between the integrated connector 212 and the thermocouple 216 and carry temperature signals from the thermocouple 216 to the integrated connector 212 so that the temperature signals can then be transmitted to the microwave generator 220 via the reusable cable assembly 200. The coaxial cable of the cable bundle 215 is connected between the integrated connector 212 and the microwave probe 218 and carries microwave power signals between the integrated connector 212 and the microwave probe 218 so that microwave power signals can then be received from the microwave generator 220 via the reusable cable assembly 200.

The fluid pump 240, which is powered by AC mains via an electrical isolation device 221, pumps the saline solution in the saline bag 242 through the cooling system 244, which includes fluid conduits, to cool the microwave probe 218.

The generator 220 includes remote temperature hardware 220 that couples to the remote temperature probe 232 to receive temperature measurements. The temperature measurements may be displayed to the clinician or may be used in a feedback loop to control characteristics of the microwave signal generated by the generator 220. The generator 220 is powered by a power supply 223, which receives AC power from electrical mains via the isolation device 221 and converts the AC power to DC power. The DC power is provided to the microwave amplifier 225 and the hardware controller 226. The hardware controller 226 controls the microwave amplifier 225 to convert the DC power to a microwave signal, which is transmitted to the microwave probe 218 via the integrated connector 228, the reusable cable assembly 200, the integrated connector 212, and the coaxial cable of the cable bundle 215.

The microwave generator 220 includes serial and parallel data ports for interfacing with the generator 220, the remote temperature probe 232, the reusable cable assembly 200, and ablation probes 210. For example, a computer may be connected to the serial port 221 to retrieve temperature data from the memory 214 of the ablation probe 210 or to retrieve temperature measurements from a temperature sensor incorporated into the double barrel connector assembly 202.

The microwave ablation system also includes a reusable cable assembly 200, which includes an integrated connector 204 for connecting to the generator 220 and the double barrel connector assembly 202.

Figure 3:
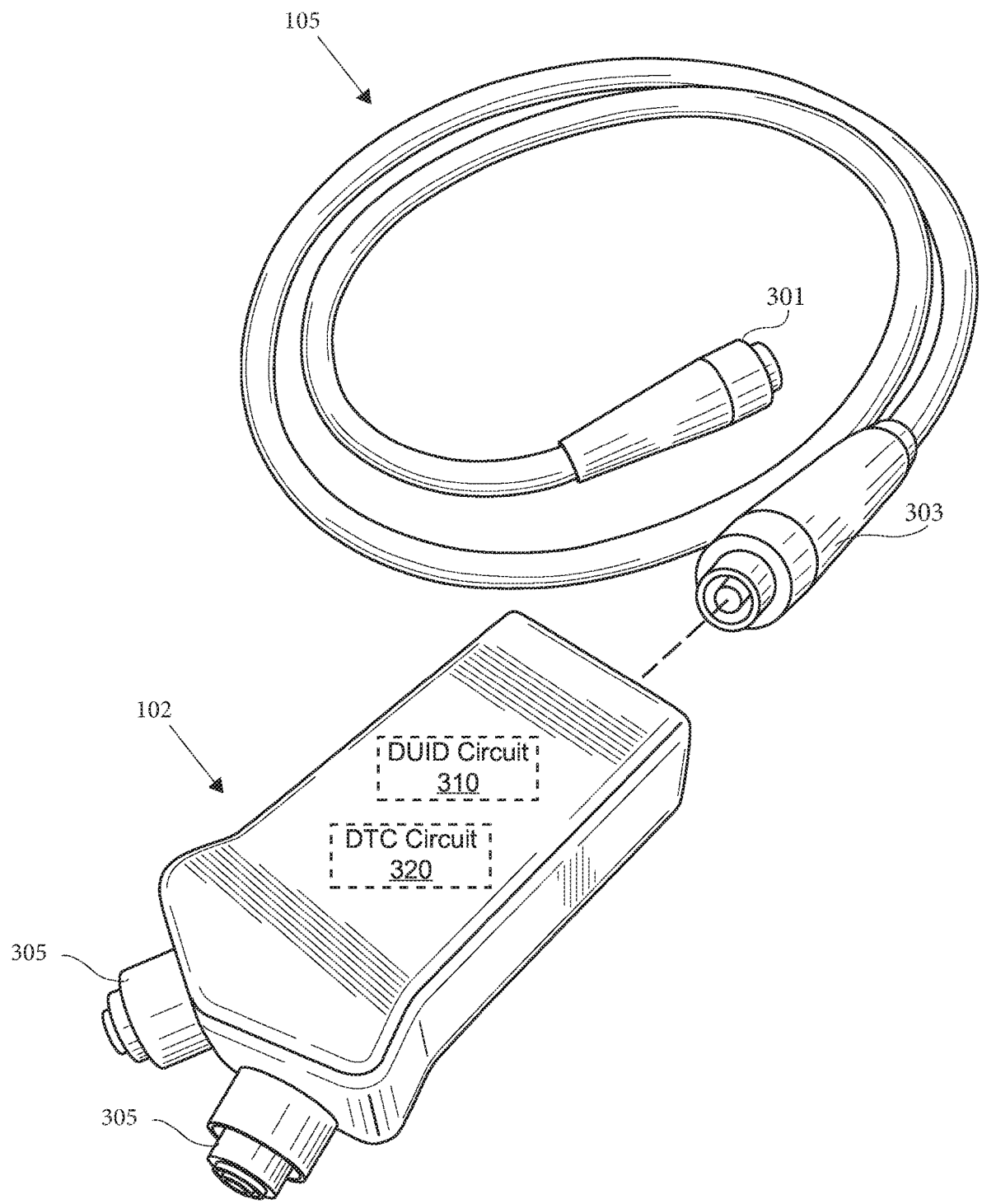
FIG. 3 is a perspective view of a double barrel connector assembly according to embodiments.

FIG. 3 is a perspective view of a two-channel cable assembly according to embodiments. The cable assembly includes a double barrel connector assembly 102 and a cable 105. The double barrel connector assembly 102 includes two microwave antenna connectors 305 for connecting to corresponding connectors of microwave antennas. The cable 105 includes a connector 301 for connecting to a corresponding connector of a microwave generator 220 and a connector 303 for connecting to a corresponding connector of the double barrel connector assembly 102. In embodiments, the connector 303 and the corresponding connector of the double barrel connector assembly 102 may be removed and the cable 105 may be permanently connected to the double barrel connector assembly 102.

In some embodiments, the double barrel connector assembly 102 divides synchronous power from the generator equally between the channels. Additionally or alternatively, the double barrel connector assembly 102 divides power from the generator unequally between the channels. An active switch may be used to divide the power equally or unequally between the two channels. A DC source may be used for controlling the active switch.

In other embodiments, a power splitter is used to divide power from the generator between the channels. The power splitter may be a miniaturized 2450 MHz, 150 W, two-way microwave power splitter module. For optimal performance, the microwave power splitter module may have high isolation, low insertion loss, and low Voltage Standing Wave Ratio (VSWR). For example, for a 2450 MHz microwave ablation system, the microwave power splitter module may have the following specifications:

| | |
|---|---|
| Frequency Range (GHz) | 2.4-2.5 |
| Amplitude Balance (max dB) | 0.25 |
| VSWR Input (max) 2.4-2.5 GHz | 1.5:1 |
| VSWR Output (max) | 1.3:1 |
| Input Power (W) Max Load VSWR 1.2:1 | 300 |
| Input Power (W) Max Load VSWR 2.0:1 | 175 |
| Insertion Loss dB (max) 2.4-2.5 GHz | 0.45 |
| Isolation dB (min) 2.4 GHz-2.5 GHz | 18 |
| Phase Balance in degrees (max) 2.4-2.5 GHz | ±5° |

The double barrel connector assembly 102 includes electrical circuitry and a power splitter disposed within the housing of the double barrel connector assembly 102. The electrical circuitry includes device unique identification (DUID) circuit 310 and a device temperature control (DTC) circuit 320. The device unique identification (DUID) circuit 310 determines whether or not the microwave antennas connected to the connectors 305 are the same or different. If the DUID circuit 310 determines that the microwave antennas are different, the DUID circuit 310 may send a signal to the microwave generator via the cable 105 disabling the microwave generator. Otherwise, if the DUID circuit 310 determines that the microwave antennas are the same, the DUID circuit 310 may send a signal to the microwave generator via the cable 105 enabling the microwave generator because the power splitter of the double barrel connector assembly will be able to split the microwave energy equally and thereby function properly. The device temperature control (DTC) circuit 320 determines which microwave antenna has the highest temperature and provides this information to the microwave generator.

Figure 4:
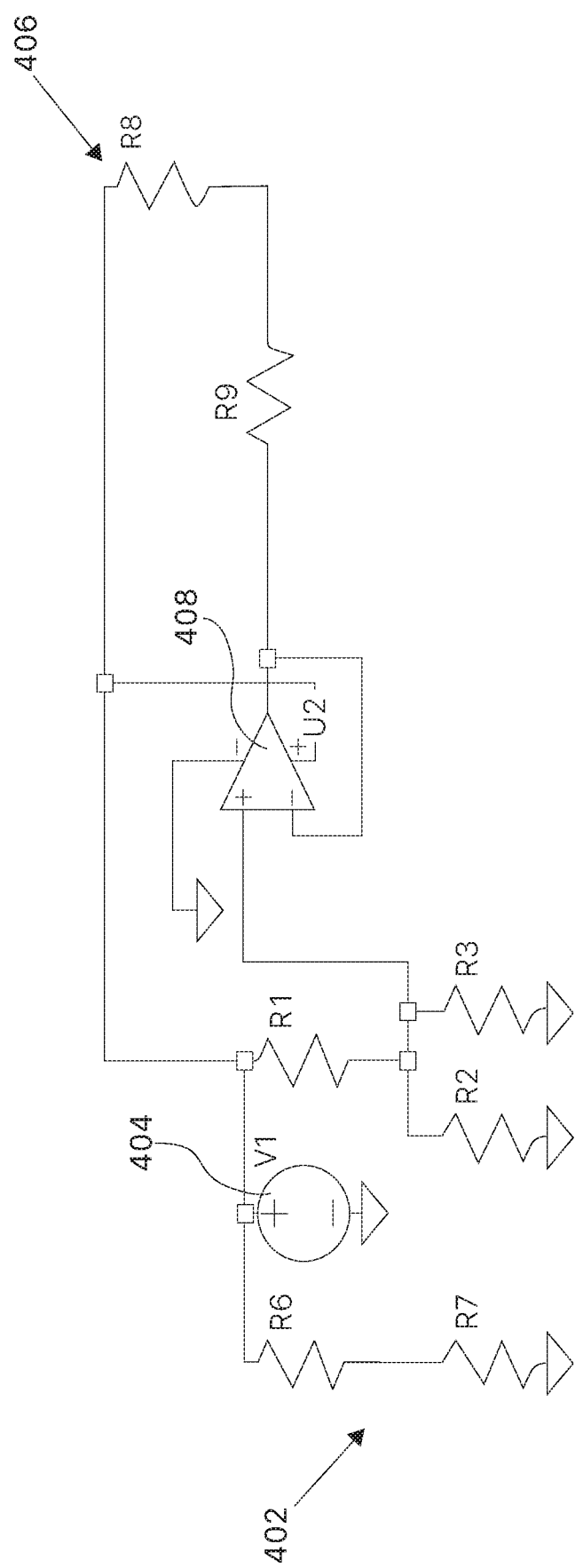
FIG. 4 is a schematic diagram of a device unique identification (DUID) circuit according to embodiments.
Figure 5:
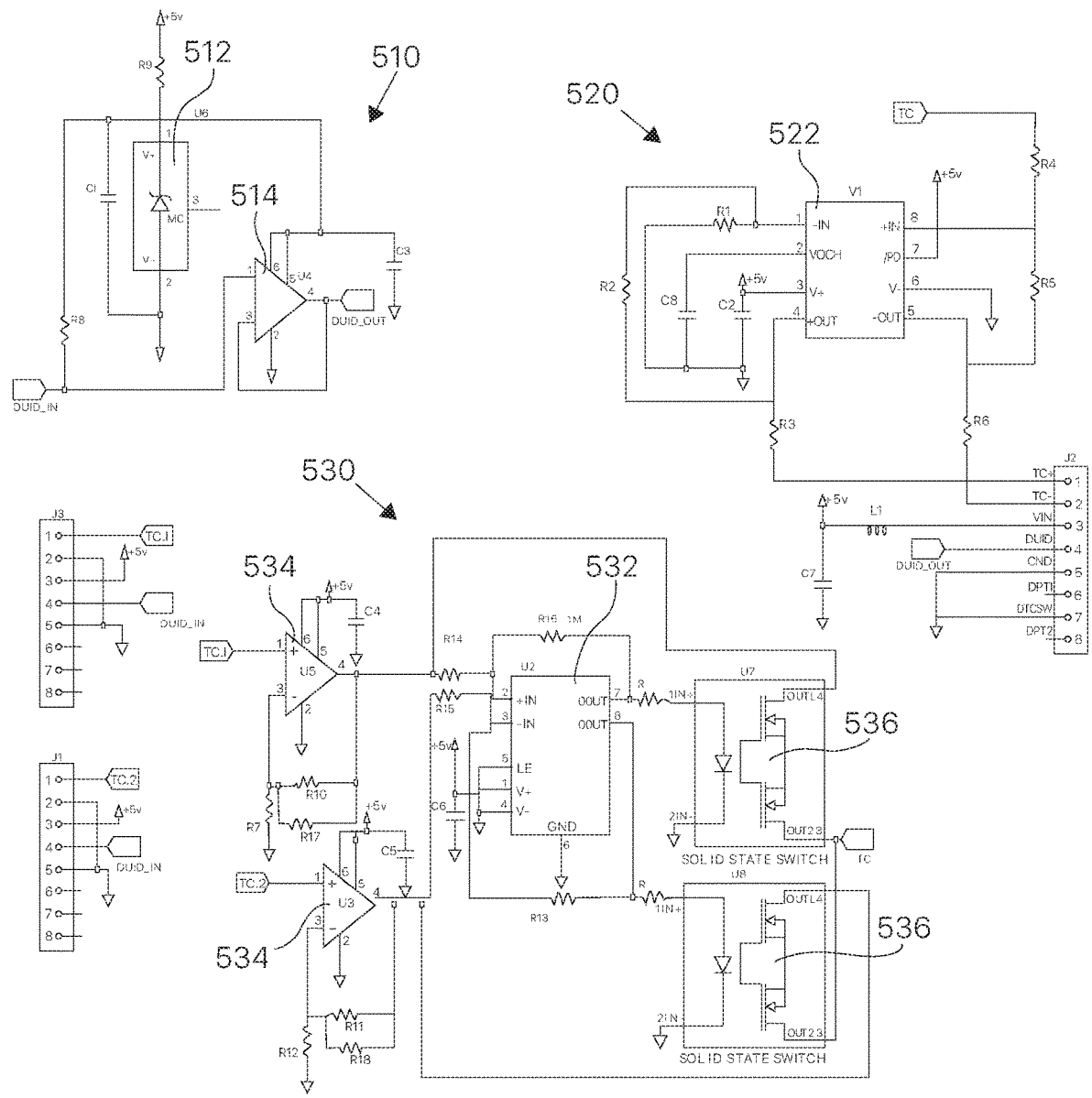
FIG. 5 is a schematic diagram of a combination of a DUID circuit and a Device Temperature Control (DTC) circuit according to embodiments.

FIGS. 4 and 5 are schematic diagrams of a double barrel connector assembly circuits according to embodiments. FIG. 4 is a device unique identification (DUID) circuit. The DUID circuit includes a differential amplifier 408 and resistors R1-R3 and R6-R9, which are arranged in such a way as to detect whether two microwave antennas connected to the power splitter module are the same or different. If both microwave antennas are the same, the microwave ablation system treats the microwave antennas as a single microwave antenna and the DUID circuit may enable the power splitter to divide the microwave power signal generated by the microwave generator equally between the microwave antennas. In an alternative embodiment, an electrically-variable power divider could be used to variably divide the power between the two or more ports (e.g., output ports 601, 602 of FIG. 6A) or the two or more microwave antennas. The electrically-variable power divider may be controlled by a processor or the generator, or may be controlled by a user via a variable slider on the housing of the double barrel connector assembly 102. The electrically-variable power divider may be used to provide larger and smaller ablative effects by each channel.

Voltage V1 is the generator voltage 404. Thus, the left side 402 of voltage V1 corresponds to an existing microwave ablation system and the right side 406 of voltage V1 corresponds to a new microwave ablation system. A resistor internal to the microwave generator is resistor R6 on the left side 402 and is resistor R8 on the right side 406. As an example, in some existing microwave ablation systems, R2=R3=R7=3000 ohms corresponds to 'short Emprint percutaneous antennas' of length 15 cm. The DUID circuit may be designed in such a way that if R2=R3=R7, then the left node between resistors R6 and R7 and the right node between resistors R8 and R9 will be at the same voltage level, in which case the microwave antennas are treated as the same microwave antennas. For each of the other combinations of R2, R3, and R7 (i.e., R2≠R3=R7, R2≠R3≠R7, etc.), there will be a specific voltage difference between the right node and the left node, in which case the microwave antennas are treated as different microwave antennas.

FIG. 5 illustrates example electrical circuitry of the connector assembly according to other embodiments. The electrical circuitry includes a DUID circuit 510 according to an alternative embodiment and device temperature control (DTC) circuitry, which includes an amplifier circuit 520 and a comparator circuit 530, that can determine which microwave antenna is at a higher temperature than the other. The comparator circuit 530 includes a comparator 532 in which the temperatures of the microwave antennas are input via respective differential amplifiers 534. The comparator circuit 530 includes an output for each input. Solid state switches 536 are connected to respective outputs of the comparator 532. The solid state switches 536 turn on and off depending upon the comparator result and provide temperature measurements to the microwave generator via the amplification circuit 520, which includes an amplifier 522.

Figure 6A:
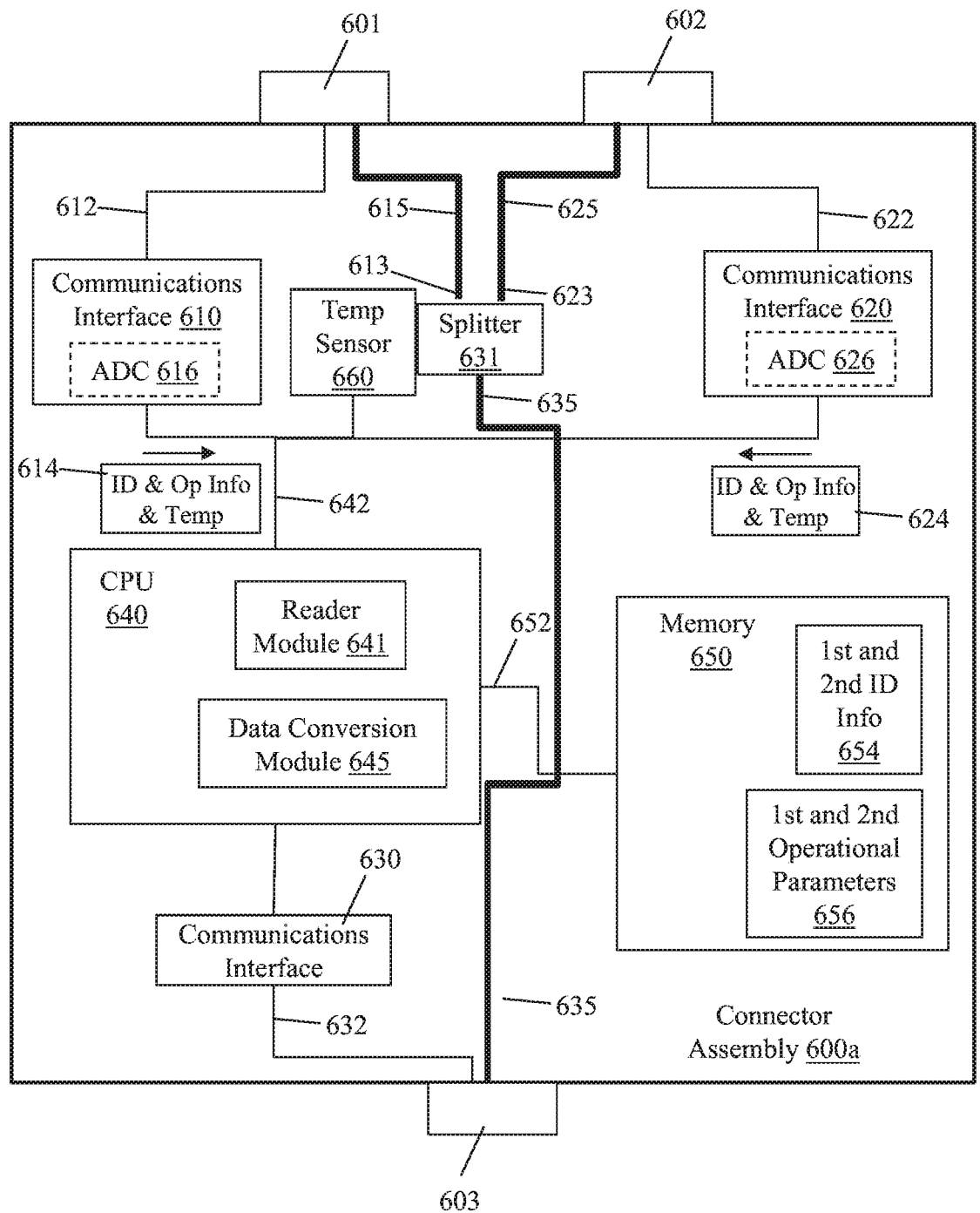
FIGS. 6A-6C are block diagrams of double barrel connector assemblies according to other embodiments.

FIG. 6A is a block diagram of a connector assembly circuit 600 according to another embodiment. The connector assembly circuit 600 includes output ports 601, 602 for connecting to respective microwave antennas and an input port 603 for connecting to a microwave generator. The connector assembly circuit 600 also includes communications interfaces 610, 620, 630. Communications interfaces 610, 620 are connected to respective output ports 601, 602 via respective electrical lines 612, 612. The communications interfaces 610, 620 transmit and/or receive digital and/or analog signals from the circuitry of microwave antennas connected to respective output ports 601, 602.

In embodiments, the communications interfaces 610, 620 may optionally include respective analog-to-digital converters (ADCs) 616, 626 for converting analog signals into digital form. In embodiments, temperature measurements or location signals may be transmitted from the microwave antennas as analog signals. For example, electrical signals produced by orthogonal coils in the microwave antennas for determining the position and/or orientation of the microwave antennas may be transmitted to the communications interfaces 610, 620. The analog signals are converted into digital form by the ADCs 616, 626.

The connector assembly circuit 600 also includes a central processing unit (CPU) 640 and a memory 650 connected to the CPU 640 via a bus 652. The communications interfaces 610, 620 transmit digital data to the CPU 640 via the bus 642. The digital data 614, 624 may include identification information, position and/or orientation information, operational information, and temperature information of the microwave antennas connected to the output ports 601, 602. The operational information may include operational parameters or settings of the microwave antennas. The digital data 614, 624 may be read by the reader module 641 of the CPU 640 from the memory incorporated into the microwave antennas that are connected to the output ports 601, 602.

In embodiments, the CPU 640 receives digital data from the communications interfaces 610, 620 and store the digital data in memory 650. For example, the CPU 640 may receive first and second identification information for respective microwave devices connected to the output ports 601, 602 from the communications interfaces 610, 620 and store the first and second identification information 654 as a data structure in memory 650. Similarly, the CPU 640 may receive first and second operational parameters for respective microwave devices connected to the output ports 601, 602 from respective communications interfaces 610, 620 and store the first and second operational parameters 656 as a data structure in memory 650. Upon receiving a request from a microwave generator connected to the input port 603, the CPU 640 may access memory 650 and provide the first and second identification information 654 and/or the first and second operational parameters 656 to the microwave generator.

In embodiments, CPU 640 can execute various applications which include instruction sets stored in memory 650. The CPU 640 may be implemented in a digital signal processor (DSP), an application specific integrated circuit (ASIC), or a field programmable gate array (FPGA).

The memory 650 can be any device, physical structure, and/or populated data structure which functions as a recorded media storage device. In some embodiments, memory 650 may include computer memory which is volatile, that is, memory which does not maintain its state when an electric current is no longer available. Memory 650 may include non-volatile memory, dynamic memory, and/or redundant memory. Examples of such memory include random access memory (RAM), optical memory devices, magnetic media, disc hard drives, solid state hard drives, SDRAM, DDR RAM, erasable programmable read-only memories (EEPROMs), or other media for storing data for future retrieval or modification. In accordance with some embodiments, memory 650 can be contained within one contiguous region of a physical device, may span across multiple regions on a physical device, or may span multiple memory devices such as virtual memory allocated within non-volatile memory space.

The CPU 640 may run a data conversion module 645 that converts the first and second information received from the communications interfaces 610, 620 into single channel information that can be transmitted to a microwave generator connected to the input port 603 via a communications interface 630 and an electrical line 632 connecting the communications interface 630 to the input port 603.

Figure 6B:
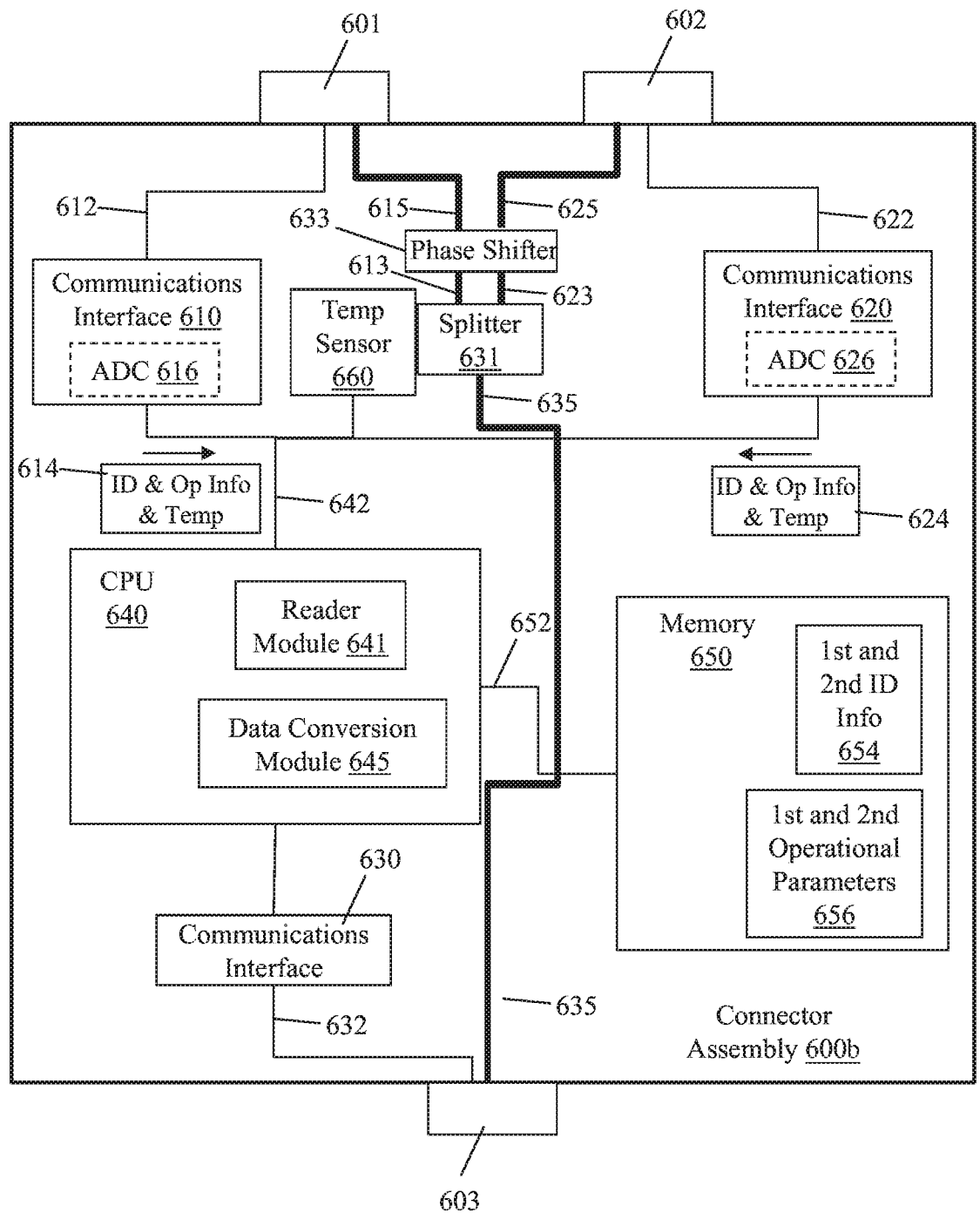

The connector assembly circuit 600 also includes a main transmission line 635 that connects to the input port 603 and to a power splitter 631. Alternatively, as shown in FIG. 6B, the power splitter 631 may be connected to a phase shifter 633 via splitter output transmission lines 613, 623. The phase shifter 633, in turn, is connected to output ports 601, 602 via phase shifter output transmission lines 615, 625. The power splitter 631 splits the microwave signal propagating through the main transmission line 635 into two microwave signals. The microwave signals may have equal or unequal power levels. The two microwave signals are then fed through the phase shifter 633, which may modify the phases of the two microwave signals. In embodiments, the phase shifter 633 may be split so as to synchronize the phases of the two microwave signals output from the power splitter 631 to obtain beneficial cooking results. The two microwave signals output from the phase shifter 633 and then fed to respective output ports 601, 602.

Figure 6C:
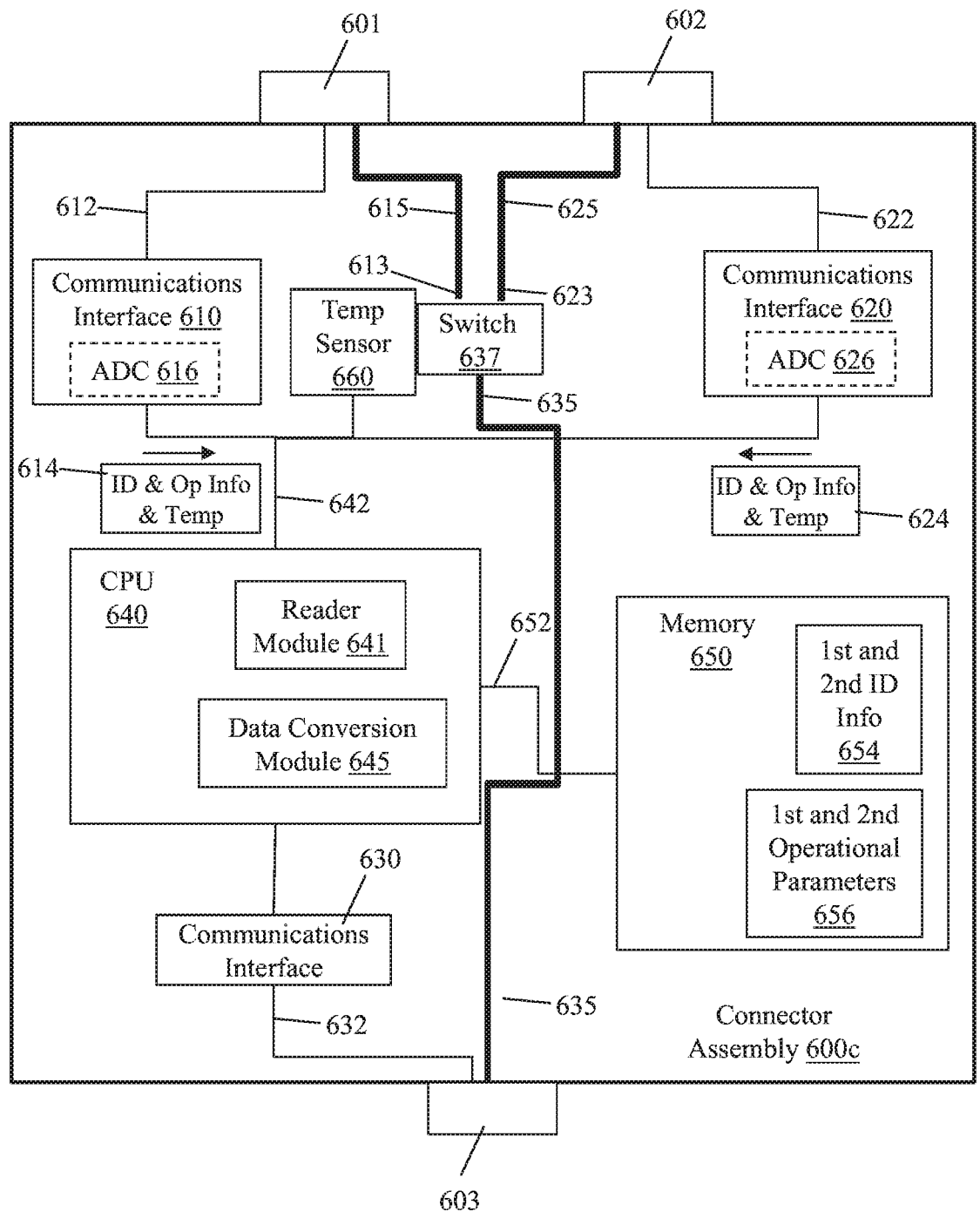

FIG. 6C is a block diagram of a connector assembly circuit 600c according to yet another embodiment. The connector assembly circuit 600c is the same as the connector assembly circuit 600a of FIG. 6A except that connector assembly circuit 600c uses a switch 637 instead of the power splitter 631 of the connector assembly circuit 600a of FIG. 6A. The switch 637 switches the microwave signal propagating through the main transmission line 635 between the output port 601 and the output port 602. The switch 637 may be a transfer switch.

The switch 637 switches between single-channel operation and two-channel operation in the event a user desires to use the connection assembly as a single-channel connection assembly. The switch 637 may be a manual switch. Alternatively, the switch 637 may be controlled by the microwave generator. For example, the switch 637 may be controlled to switch between output port 601 and output port 602 during energy delivery to divide the generator power into the two channels through time multiplexing. The generator power may be divided equally or unequally between output port 601 and output port 602 by adjusting the switching duty cycle of the generator. For example, with a switching duty cycle of 50%, equal energy would be provided to each channel. As another example, with a switching duty cycle of 60%, 60% of the energy would be delivered to output port 601 and 40% of the energy would be delivered to output port 602.

Figure 7:
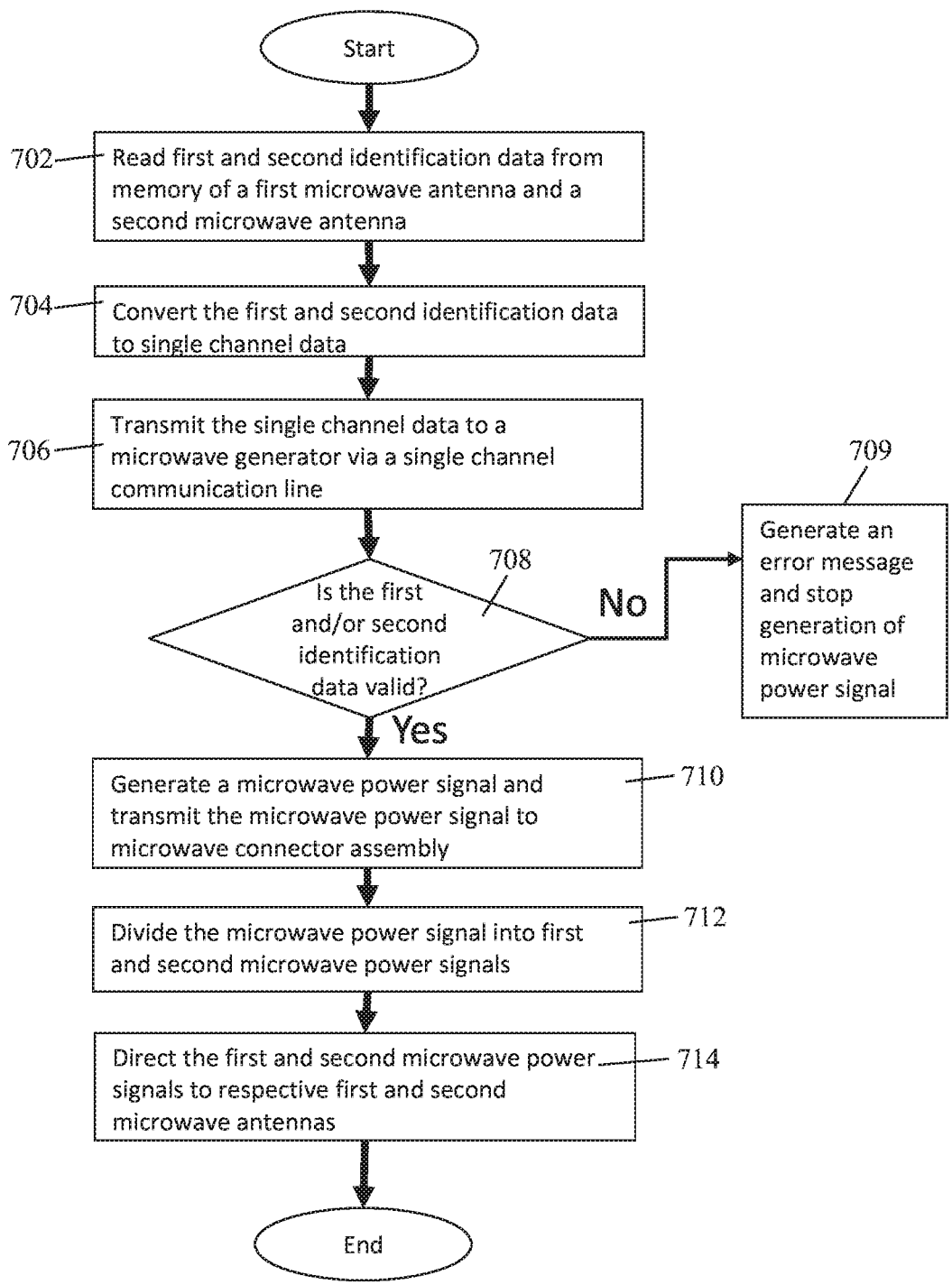
FIG. 7 is a flow diagram illustrating an example process performed by a microwave generator system in accordance with embodiments.

FIG. 7 is a flow diagram illustrating a method of reading identification data from multiple microwave antennas via a single channel of a generator according to embodiments. After starting, first identification data is read from memory of a first microwave antenna and second identification data is read from memory of the second microwave antenna at block 702. In embodiments, the memory may be an EPROM, in which case identification data would be read from the EPROM by providing identification data address values at the address pins of the EPROM and obtaining the identification data values at the output buffer of the EPROM. At block 704, the first and second identification data is converted to single channel data. For example, the first identification data may be inserted into a first field of the single channel data and the second identification data may be inserted into a second field of the single channel data. The single channel data may include other fields describing the data in the first and second fields so that the microwave generator can properly interpret the single channel data and extract the first and second identification data from the single channel data.

In an alternative backward compatible embodiment, the processor determines what device information to present to the analog generator based upon the detected devices connected to output ports 601 and 602. The processor may condition the device information into two or more analog signals, which are transmitted to analog communication lines via the input port 603. The communications interface 630 may include a digital-to-analog converter (DAC) to convert the device information into the two or more analog signals. The communications interface 630 may then transmit the two or more analog signals to an analog microwave generator via the analog communication lines. In example embodiments, the communications interface 630 may communicate the temperature of a first device on a first analog communication line using a first DC voltage level and may communicate the type of the first device on the same analog communication line using a second DC voltage level. Similarly, the communications interface 630 may communicate the temperature of a second device on a second analog communication line using a first DC voltage level and may communicate the type of the second device on the same analog communication line using a second DC voltage level.

At block 706, the single channel data is transmitted to the microwave generator via a single channel communication line(s) within the cable attached to the two-port connector assembly. After extracting the first and second identification data, the microwave generator determines whether the first and second identification data is valid at block 708. If the first and/or second identification data is determined to be invalid, an error message is generated and the generation of a microwave power signal is stopped at block 709.

If the first and/or second identification data is determined to be valid, a microwave power signal is generated and transmitted to the microwave connector assembly at block 710. At block 712, the microwave power signal is divided into first and second microwave power signals and, at block 714, the first and second microwave power signals are directed to the first and second microwave antennas, respectively.

Figure 8:
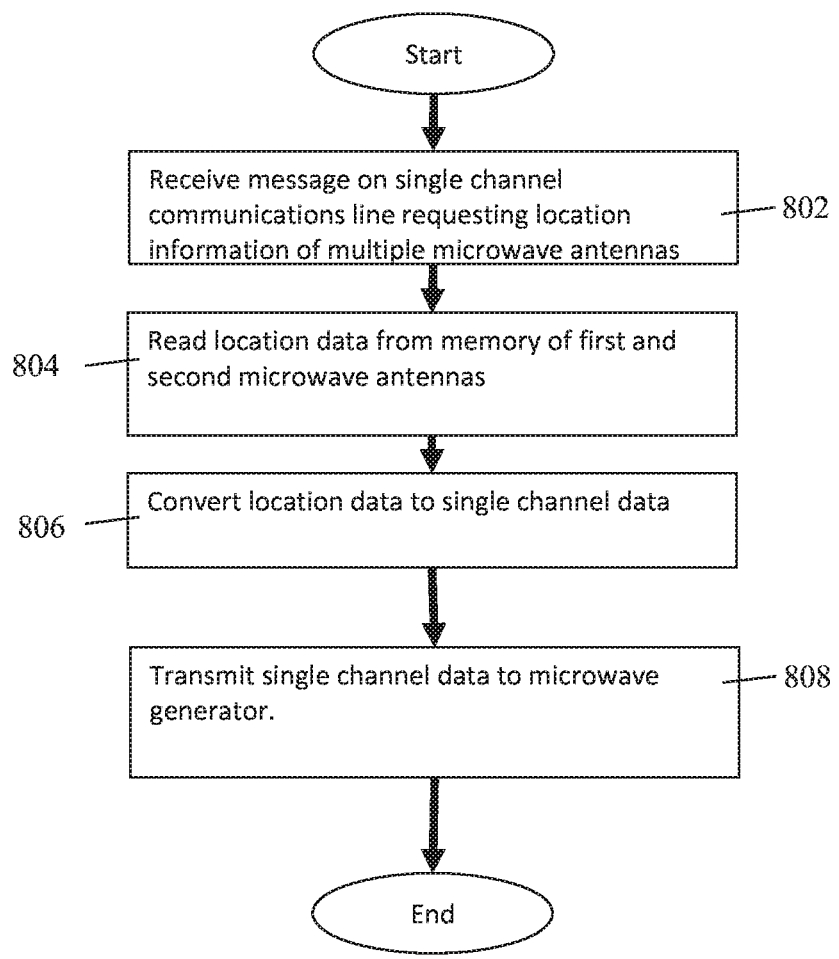
FIG. 8 is a flow diagram illustrating an example process performed by the double barrel connector assembly in accordance with embodiments.

FIG. 8 is a flow diagram illustrating a method of obtaining location data from multiple microwave antennas via a single channel of a generator according to embodiments. After starting, a message is received on a single communication line requesting location data of multiple microwave antennas at block 802. The message may include the identification numbers of the microwave antennas and address information for reading location data from the memory disposed on each microwave antenna. At block 804, location data is read from the memory of each microwave antenna connected to the ports of the microwave connector assembly by providing address values at the address pins of the memory and obtaining location data values at the output pins of the memory.

At block 806, the read location information is converted into single channel location data. For example, the processor of the connector assembly may create a data packet that includes the read location data for the microwave antennas and identification numbers for identifying which portion of the read location data corresponds to each of the microwave antennas. In embodiments, the read location data of each microwave antenna may be associated with the identification number of that microwave antenna in the data packet. At block 808, the single channel location data is transmitted to the microwave generator, which may extract the read location data from the single channel location data and use the read location data to perform a function related to the ablation procedure. For example, the read location data may be used in a navigation system for navigating microwave antennas through the anatomy of a patient.

Figure 9:
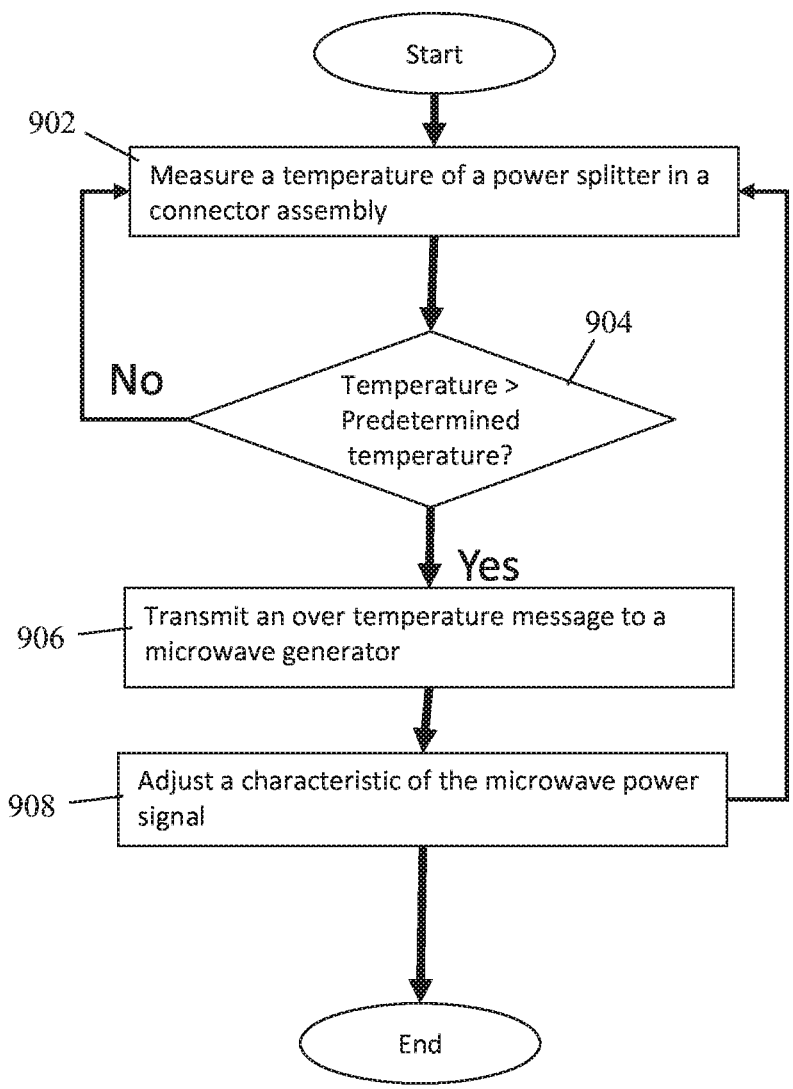
FIG. 9 is a flow diagram illustrating an example process for controlling the temperature of the double barrel connector assembly in accordance with embodiments.

FIG. 9 is a flow diagram illustrating a method of controlling the temperature of a connector assembly according to embodiments. After starting, a temperature of a power splitter in the connector assembly is measured at block 902. The temperature may be measured by digitally sampling a temperature reading from a thermocouple or other appropriate temperature sensor disposed on or in the connector assembly. In embodiments, the temperature may be measured over a period and averaged to ensure accuracy of the temperature measurement.

At block 904, the measured temperature is compared to a predetermined temperature indicative of an over-temperature condition to determine whether the measured temperature is greater than the predetermined temperature. The predetermined temperature may be near a temperature at which harm could be caused to the connector assembly electronics. If the measured temperature is greater than the predetermined temperature, an over-temperature message is transmitted to a microwave generator at block 906. The over-temperature message may include instructions to adjust settings of the microwave generator or to adjust a characteristic of the microwave energy generated by the microwave generator. The over-temperature message may be a voltage level or may include alpha-numeric characters.

At block 908, a characteristic of the microwave power signal is adjusted to remove the over-temperature condition and the method returns to block 902. For example, the duty cycle of the microwave power signal may be decreased to decrease the amount of microwave energy delivered to the microwave antennas. If the measured temperature is not greater than the predetermined temperature, the method returns to block 902 to repeat the process of monitoring for and appropriately responding to an over-temperature condition.

In some embodiments, the double barrel connector assembly and/or the microwave antennas may be configured as "smart" devices. Each smart device may use an identification resistance. For example, the smart device identification resistance for the double barrel connector assembly may be 1690 ohms. The generator may measure this resistance and identify the double barrel connector assembly as a smart accessory. The generator may communicate with the double barrel connector assembly using a suitable communications protocol to obtain information relating to the double barrel connector assembly and/or one or more of the microwave antennas connected to the double barrel connector assembly.

The information relating to the double barrel connector assembly and/or one or more of the microwave antennas connected to the double barrel connector assembly may include at least one of device-specific limits, device-specific capabilities, device state, device lot number, and device miscellaneous information. The device-specific limits may include at least one of a maximum set power, a maximum treatment time, a maximum device pre-check temperature, a maximum device temperature, and a maximum reflected power. The device-specific capabilities may include at least one of a microwave activation/deactivation capability and a microwave set power capability. The device state may include at least one of a microwave activation/deactivation request state (e.g., the smart device is requesting microwave activation or the smart device is requesting microwave deactivation), a state in which a smart device requested set power as a percentage of maximum set power, and a smart device general status (e.g., a state in which the smart device has encountered a general error). The smart device miscellaneous information may include at least one of a disposable reuse count, a device reuse count, antenna identification, and antenna loss information.

According to an example communications protocol, the data packet may include a header (e.g., a uniquely identifiable header that cannot naturally occur in the data payload), a data payload, and a checksum (e.g., a logical summation of the bytes in the header and data payload). The header information may indicate that the data packet is directed from the generator to the smart device, that the data packet is directed from the smart device to the generator, or that the data packet is directed from the smart device to the generator and the smart device detected an error (e.g., a checksum error). The data payload of the data packet transmitted from the microwave generator to the double barrel connector assembly may include a request for at least a portion of the information relating to the double barrel connector assembly and/or one or more of the microwave antennas connected to the double barrel connector assembly. The data payload of the data packet transmitted from the double barrel connector assembly to the microwave generator may include the at least a portion of the information relating to the double barrel connector assembly and/or one or more of the microwave antennas connected to the double barrel connector assembly.

The data payload may also identify the smart device or smart devices, e.g., a microwave antenna, to which the device information relates. For example, the microwave generator may transmit a data packet to the double barrel connector assembly in which the bytes of the data payload are set to request a microwave power level, an activation state, and an error state of the double barrel connector assembly. As another example, in response to a request from the microwave generator, the double barrel connector assembly may transmit a data packet, in which the data payload includes the temperature of the double barrel connector assembly or two or more multiplexed temperature measurements within the double barrel connector assembly, to the microwave generator.

In some embodiments, the microwave generator may transmit a data packet to the double barrel connector assembly requesting information relating to a specified microwave antenna of two or more microwave antennas connected to the double barrel connector assembly. In response, the double barrel connector assembly may create or generate a response data packet including the requested information relating to the specified microwave antenna of the two or more microwave antennas.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope and spirit of the claims appended hereto. For example, while the present disclosure makes reference to microwave ablation, the present disclosure contemplates application of the systems and methods to other types of energy-based surgical techniques.

The invention claimed is:

1. A cable assembly, comprising:
   a microwave transmission line;
   a signal divider network coupled to an end portion of the microwave transmission line and including at least two ports;
   an electrical line; and
   a monitoring circuit coupled to the electrical line and configured to receive at least first and second device information via the at least two ports, respectively, and convert the at least first and second device information to single channel information.

2. The cable assembly of claim 1, wherein the cable assembly is a reusable cable assembly.

3. The cable assembly of claim 1, wherein the signal divider network includes a power splitter.

4. The cable assembly of claim 3, further comprising a phase shifter configured to shift phases of at least two microwave signals output from the respective at least two ports of the signal divider network.

5. The cable assembly of claim 4, wherein the phase shifter is configured to shift the phases of the at least two microwave signals so that the at least two microwave signals are in phase.

6. The cable assembly of claim 3, further comprising a temperature sensor configured to measure the temperature of the power splitter,
    wherein the monitoring circuit is in communication with the temperature sensor and is configured to monitor the temperature of the power splitter and transmit a power splitter temperature message to a microwave generator if the temperature of the power splitter exceeds a predetermined temperature threshold.

7. The cable assembly of claim 6, wherein the power splitter is a passive power splitter configured to divide microwave energy equally between the at least two ports.

8. The cable assembly of claim 1, wherein the first and second device information includes identification information and status information corresponding to the devices coupled to the at least two ports.

9. The cable assembly of claim 8, wherein the status information includes temperature of each of at least two microwave antennas coupled to the at least two ports.

10. The cable assembly of claim 1, wherein the single channel information is backward compatible with a single channel generator.

11. The cable assembly of claim 1, further comprising a switch configured to switch between a single channel cable and a double channel cable.

* * * * *